United States Patent [19]

Yanami et al.

[11] Patent Number: 4,683,297
[45] Date of Patent: Jul. 28, 1987

[54] PROCESS FOR THE PREPARATION OF GLYCOSIDES

[75] Inventors: Tetsuji Yanami; Yoshiyuji Murai, both of Himeji; Ryoichi Oshima, Tokyo, all of Japan

[73] Assignee: Daicel Chemical Industries Ltd., Osaka, Japan

[21] Appl. No.: 834,669

[22] Filed: Feb. 28, 1986

Related U.S. Application Data

[63] Continuation of Ser. No. 617,353, Jun. 5, 1984, abandoned.

[30] Foreign Application Priority Data

Jun. 7, 1983 [JP] Japan ................................ 58-100254
Jun. 10, 1983 [JP] Japan ................................ 58-102711

[51] Int. Cl.$^4$ ............................................. C07H 1/00
[52] U.S. Cl. ..................................... 536/18.6; 536/4.1
[58] Field of Search ............................... 536/4.1, 18.6

[56] References Cited

U.S. PATENT DOCUMENTS

| | | |
|---|---|---|
| 3,547,828 | 12/1970 | Mansfield et al. ................... 536/4.1 |
| 3,598,865 | 8/1971 | Lew ..................... 536/4.1 |
| 3,772,269 | 11/1973 | Lew ..................... 536/4.1 |
| 4,464,204 | 8/1984 | Niekamp et al. ................... 536/18.6 |
| 4,465,221 | 8/1984 | Seidman et al. ................... 536/18.6 |

*Primary Examiner*—Johnnie R. Brown
*Assistant Examiner*—Elli Peselev
*Attorney, Agent, or Firm*—Sheldon Palmer

[57] ABSTRACT

A process for the preparation of glycosides such as methyl glucoside, butyl glucoside or the like in which a mono- or poly-saccharide is reacted with a mono- or polyhydric alcohol in the presence of a perfluorosulfonic acid resin as the catalyst.

16 Claims, No Drawings

PROCESS FOR THE PREPARATION OF GLYCOSIDES

This application is a continuation of application Ser. No. 617,353, filed June 5, 1984, now abandoned.

BACKGROUND OF THE INVENTION

1. Field of the Invention

The present invention relates to a process for the preparation of glycosides. More particularly, it relates to a process for preparing glycosides efficiently from monosaccharides or polysaccharides without the need for using a large amount of acid catalysts.

2. Description of the Prior Art

Glycosides are very valuable as the starting material for glycoside polyethers which are used for the preparation of polyurethane foams (for instance, reference is made to U.S. Pat. No. 4,359,573, U.S. Pat. No. 4,366,265, U.S. Pat. No. 4,342,864, Modern Plastics International Aug. 1982, page 45, etc.). Glycoside compounds in which the saccharide portion is constituted by glucose are known in general as glucosides and they are useful as the starting material for cosmetics (for instance, see U.S. Pat. No. 4,323,468). Above all, methyl glucoside is particularly important (see Soap, Perfumery & Cosmetics, 47 (9), 406 (1974), U.S. Pat. No. 4,324,703, etc.). Methyl glucoside is also useful as a plasticizer for thermo-setting resins (see, Japanese Patent Publn. No. Sho 50-13770).

Up to the present, many processes for synthesizing such compounds have been reported. As representative examples, there can be mentioned.

(i) processes for the preparation of glycosides using hydrochloric acid as catalyst [Organic Synthesis, Collective Vol. (I) 364 (anhydroglucose is used as the starting material), Cantor et al. U.S. Pat. No. 2,390,507 (starch is used as the starting material). Roudier et al. FRP No. 1114382 (starch is used as the starting material)], (ii) processes for the preparation of methyl glucoside using sulfuric acid as catalyst [Langlois U.S. Pat. No. 2,276,621 (starch is used as the starting material)], (iii) processes using a Lewis acid as catalyst [Kaiser et al. U.S. Pat. No. 3,296,245 (starch is used as the starting material)], (iv) processes for the preparation of glycosides using a cation exchange resin as catalyst [Cadotte et al. J. Amer. Chem. Soc., 74, 1501 (1952) (glucose is used as the starting material, and Amberlite IR-120 is used as the ion-exchange resin), Dean et al. U.S. Pat. No. 2,606,186 (glucose is used as the starting material, and Dowex 50, Duolite C-3, Amberlite IR-100, Zeo-Karb H or Nalcite HCR is used as the ion-exchange resin)], (v) processes for the preparation of glycosides using a water-soluble sulfonic acid [Nevin et al. U.S. Pat. No. 3,375,243 (starch is used as the starting material), Roth et al. U.S. Pat. Nos. 4,223,129 and 4,329,449 (starch is used as the starting material, in both patents)], and so on.

Thus, many varied processes are known for the preparation of glycosides, and mineral acids are widely used as catalyst. Above all, hydrochloric acid is the most popular one. This is because the molecules of mineral acids, particularly hydrochloric acid, are small and accordingly the numbers of hydrogen ions per unit volume of acid are enormous. That is, they are very effective as acid catalyst. However, mineral acids are remarkably corrosive and require the use of acid proof apparatuses. In particular, highly volatile acids such as hydrochloric acid have a disadvantage in that they injure other apparatuses in the plant by gases escaping from them.

Such defect is common also to Lewis acids. Although reactions using a water-soluble sulfonic acid considerably ease the above-mentioned disadvantage, they have the disadvantage that an elevated temperature of 140° C. or higher is required generally and the reaction mixture is considerably colored.

Moreover, in every case using one of the above-mentioned acids, the acid remains in the reaction system and so steps for neutralizing it and removing their salts are required.

To overcome these defects, processes using a cation exchange resin are recommended. However, cation exchange resins are generally inferior in their thermostability and accordingly it is impossible to effect reactions using them at an elevated temperature. The reactions are usually carried out at a lower temperature of 100° C.–110° C. and, as a matter of course, require a relatively long time (approximately 2 hours). Further, there is also a defect that the reaction system is deeply colored.

SUMMARY OF THE INVENTION

The present invention provides a process for the preparation of glycosides which comprises reacting a monosaccharide or a polysaccharide with a monohydric alcohol or a polyhydric alcohol in the presence of a perfluorosulfonic acid resin to obtain a glycoside.

DESCRIPTION OF THE PREFERRED EMBODIMENT

Among the monosaccharides used as the starting material, there may be mentioned hexoses such as glucose, mannose, galactose, etc., pentoses such as arabinose, xylose, ribose, etc., and the like. Among the polysaccharides used as the starting material, there may be mentioned those carbohydrates which are capable of producing a monosaccharide by hydrolysis, more concretely, maltose, cellobiose, sucrose, lactose, other disaccharides, oligosaccharide, dextrin, starch, cellulose, and the like. Glucose, dextrin, starch and cellulose are preferred as the starting material.

As the perfluorosulfonic acid resins used according to the present invention, there may be mentioned representative a copolymer of tetrafluoroethylene and perfluoro-3,6-dioxa-4-methyl-7-octenesulfonic acid having general formula (I):

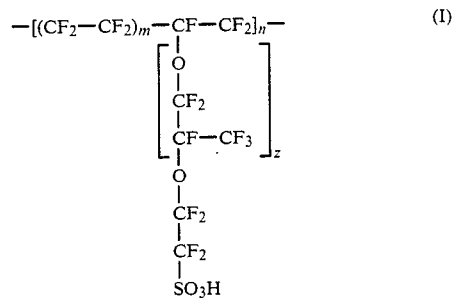

(wherein m is 5–13.5, n is approx. 1,000 and Z is 1,2,3 . . .,)

which is commercially available from du Pont under the trademark "NAFION ®". Also, other perfluorosulfonic acid resins disclosed in U.S. Pat. Nos. 4,041,090 and 4,052,474 may be employed in the present invention.

Among the monohydric alcohols used in the present invention, may be mentioned those having from 1 to 8 carbon atoms, such as methyl alcohol, ethyl alcohol, propyl alcohol, isopropyl alcohol, butyl alcohol, amyl alcohol, 2-ethylhexyl alcohol, phenol, octyl alcohol and the like. Suitable polyhydric alcohols are ethylene glycol, propylene glycol, butylene glycol, glycerol, and the like.

According to the process of this invention the intended product may be obtained in every case as described in the following:

The product is obtained by a process (1) wherein a monosaccharide or a polysaccharide is reacted with an alcohol in the presence of a perfluorosulfonic acid resin by heating and, after cooling, the sulfonic acid resin is filtered off to give a glycoside solution. The recovered resin may be used repeatedly. The glycoside may be obtained by evaporating the alcohol and adding water, in the form of an aqueous glycoside solution. As the case may be, the glycoside may be separated as crystals directly from the alcoholic solution by condensing it to some degree. For the purpose of purification, the saccharide remaining in the glycoside in a very minor amount may be removed or, as the case may be, the glycoside may be decolored by treatment with active carbon or the like.

The reaction may be performed by, as well as the abovementioned batch process, a continuous process (2) wherein a monosaccharide or a polysaccharide suspended in an alcohol is pumped into a column filled with a perfluorosulfonic acid resin, the reaction system is heated under such conditions as the reactants are kept in good contact with each other, and the reaction mixture is drawn from the bottom of the column to give a glycoside solution.

The above-mentioned process (1) is the representative embodiment of the present invention, and it is desirable to carry out the reaction in a tightly closed reaction vessel under increased pressure. It is preferred to use a pressure-resistant vessel such as an autoclave.

In the present invention, the amount of the alcohol to be used in relation to the saccharide may be varied over a wide range, depending on the individual reaction components used. Usually, the alcohol is used in excess of the amount required to react with the saccharide. This is because an excessive alcohol is required to shift the equilibrium in the reaction system so that the once formed glycoside does not revert to the saccharide as a result of hydrolysis by the water existing in the system. Here, the water existing in the system means both the moisture contained in the saccharide and the water formed from the monosaccharide by glycosidation reaction. Further, an excessive alcohol is necessary to prevent precipitation from the solution of the glycoside formed by the reaction. Generally speaking, the molar ratio of alciohol to saccharide may vary from 3:1 to 50:1, depending on the system used. As described above, the glycosidation reaction is reversible and thus, if water exists in the reaction mixture, formation of glycoside is impeded. Therefore, it is preferable to use anhydrous starting materials. However, it is not indepensable that the starting materials are anhydrous. Even with a saccharide having a moisture content of approx. 12%, a satisfactory result is obtained.

To explain further in detail, first of all, monosaccharide or a polysaccharide, a perfluorosulfonic acid resin in an amount from 1 to 100% by weight, preferably from 5 to 20% by weight, in relation to the amount of the saccharide, and an alcohol in an amount from 3 to 50 per mol of, saccharide, are introduced into a reaction vessel. When the reaction is performed under increased pressure, a pressure-resistant vessel such as an autoclave is used as described above. When an alcohol having a high boiling point, such as ethylene glycol, propylene glycol, glycerol, phenol, etc. is used, it is preferable to carry out the reaction under reduced pressure with heating, while letting the water inside the system flow out of the system. The perfluorosulfonic acid resin used in the reaction may be in the form of either cube or powder. However, it is preferable to use a pulverized resin. The catalyst may be used in a ratio extending over a wide range, in accordance with the components used.

Now, as an embodiment of the present invention, a process for the preparation of methyl glucoside is explained. In an autoclave, 50 parts by weight of glucose, 5 parts of powdery perfluorosulfonic acid resin and 133 parts of methyl alcohol are charged, and the reaction is effected at 120° C. for 30 minutes under stirring. Then the pressure in the system is 5.5–6.0 Kg/cm$^2$ (gauge pressure). After cooling to room temperature, the perfluorosulfonic acid resin is separated by filtration to obtain methyl glucoside solution. The reaction mixture is colorless and transparent, and no deterioration can be observed on the perfluorosulfonic acid resin. The perfluorosulfonic acid resin may be used again.

Although the reaction mixture is generally colorless and transparent when a monosaccharide such as glucose is used, it is usually colored in many cases when a polysaccharide such as dextrin, starch, etc. is used as the starting material because a high temperature is required to complete the reaction. Therefore, in order to obtain a colorless glycoside solution, it is preferable to use a monosaccharide as the starting material. When a polysaccharide is used as the starting material, it is desirous to add 1–2.5% by weight of a mineral acid such as hydrochloric acid, sulfuric acid, etc. per dry weight of the polysaccharide. The effect of adding such a mineral acid is that the hydrolysis of the polysaccharide into the corresponding monosaccharide is accelerated, the total reaction time is shortened and the coloring of the product is reduced.

The reaction time of the process of this invention may vary depending on the starting materials used and the reaction temperature employed. In general, a reaction time of 10 minutes to 3 hours is suitable and a reaction temperature higher than the boiling point of the alcohol used but not exceeding 230° C. is suitable.

After completion of the reaction, the resin is separated by filtration, the excess alcohol is removed from the alcoholic solution of glycoside and then water is added whereby an aqueous solution of the glycoside is obtained as the product. By regulation of the amount of the water to be added, the solid content may be adjusted to give an aqueous glycoside solution suited to the purpose. As the case may be, decoloring and purification may be effected by means of active carbon etc.

It has been found by mass spectrographic analysis that, in general, the crude glycoside does not consist of a single ingredient but contains, besides the glycoside monomer, minor amounts of its dimer, trimer and tetramer. When the main product is good crystalline one, the glycoside may be crystallized directly from the alcoholic solution by concentrating the latter to some degree. When only the pure crystalline main product is desired, the mother liquor may be recycled.

According to the present invention, the problem of corrosion due to the use of a large amount of acid catalyst, the mixing in of the acid into the reaction system and the neutralization step attendant thereon are overcome and, moreover, the perfluorosulfonic acid resin catalyst can be used repeatedly without any significant coloring of the reaction mixture and any influence on the reaction yield. Therefore, the desired glycoside such as an alkyl glycoside, such as methyl glycoside, ethyl glycoside, glycol glycoside, etc. or an aryl glycoside, such as phenyl glycoside etc. can be obtained very economically on an industrial scale.

The present invention is further explained by giving Examples. These Examples, however, are illustrative and do not limit the present invention.

EXAMPLE 1

In an autoclave of 300 cc volume, 50 g of anhydrous crystalline glucose, 5 g of perfluorosulfonic acid resin ("NAFION" powder 511) and 133 g of methyl alcohol were charged. The reaction was effected at 120° C.±1° C. for 30 minutes while stirring at 600 r.p.m. The gauge pressure was 6.0 Kg/cm². After cooling to room temperature, NAFION was separated by filtration whereby a colorless, transparent methanolic solution was obtained. By adding water and evaporating methanol at 40° C. under reduced pressure, an aqueous methyl glucoside solution was obtained. The aqueous solution was essentially colorless and transparent and 53.6 g of solid matters were contained therein. By liquid chromatography and enzymatic method, the composition of the solid matters was found to be the following:

|  | | molar yield | |
|---|---|---|---|
| methyl-α-glucoside | 55.0% by weight | 54.7 mol % | ⎫ 86.1 |
| methyl-β-glucoside | 31.6% by weight | 31.4 mol % | ⎬ mol % |
| methyl-α-maltoside & methyl-β-maltoside | 8.1% by weight | 8.8 mol % | ⎭ |
| dextrose | 2.87% by weight | 3.1 mol % | |
| ash | 0.08% by weight | | |
| higher oligoside, and others | 2.35% by weight | | |
|  | 100.0% | | |

It was found by mass spectrography that the higher oligoside was a mixture of methyl maltotrioside and methyl maltotetraoside.

EXAMPLE 2

Using 50 g of anhydrous crystalline glucose, 5 g of perfluorosulfonic acid resin ("NAFION") and 133 g of methyl alcohol, the reaction was effected in the same manner as in Example 1. The recovered NAFION was used repeatedly up to 5 times. Neigher reduction of activity nor deterioration of the NAFION were observed.

| | molar yield | | | | |
|---|---|---|---|---|---|
| | 1st time | 2nd time | 3rd time | 4th time | 5th time |
| ethyl-α-glucoside | 55.3 | 52.7 | 52.1 | 55.3 | 55.4 |
| methyl-β-glucoside | 31.0 | 33.5 | 34.7 | 33.0 | 32.3 |
| methyl-α-maltoside & methyl-β-maltoside | 8.88 | 8.1 | 9.8 | 8.7 | 7.3 |

EXAMPLE 3

In an autoclave, 54.0 g of corn dextrin (containing 12% of moisture), 2.0 g of "NAFION" powder and 133 g of methyl alcohol were reacted at 160° C.±1° C. for 30 minutes while stirring at 600 r.p.m. The pressure was 16±0.4 Kg/cm² (gauge pressure). After cooling, NAFION was separated by filtration whereby a brown colored liquor was obtained. The yield was as follows:

| | molar yield |
|---|---|
| methyl-α-glucoside | 52.7 mol % |
| methyl-β-glucoside | 29.0 mol % |
| methyl-α-maltoside & methyl-β-maltoside | 8.9 mol % |
| dextrose | 2.8 mol % |
| higher oligoside, ash, and others | 6.6 mol % |

EXAMPLE 4

In an autoclave, 50.0 g of commercially available corn starch (containing 12% of moisture), 4.4 g of "NAFION" powder and 130 g of methyl alcohol were reacted at 140°–145° C. for 2 hours while stirring. A slightly brown colored glucoside solution was obtained, after separation of 4.4 g of "NAFION" and 3.1 g of unreacted starting material by filtration. The yield was as follows:

| | molar yield |
|---|---|
| methyl-α-glucoside | 48.6 mol % |
| methyl-β-glucoside | 26.5 mol % |
| methyl-α-maltoside & methyl-β-maltoside | 7.2 mol % |
| dextrose | 2.0 mol % |

EXAMPLE 5

In an autoclave, 54.9 g of potato starch (containing 19.8% of moisture), 2.0 g of "NAFION" powder and 133 g of methyl alcohol were reacted at 160° C.±2° C. for 2.5 hours while stirring. The pressure was 16.5±1.0 Kg/cm² (gauge pressure). After separation of "NAFION" and unreacted starting material (3.62 g) by filtration, a yellow colored glucose solution was obtained. The yield was as follows:

| | molar yield |
|---|---|
| methyl-α-glucoside | 45.5 mol % |
| methyl-β-glucoside | 26.7 mol % |
| methyl-αmaltoside & methyl-β-maltoside | 8.8 mol % |
| dextrose | 3.6 mol % |

EXAMPLE 6

In an autoclave of 300 cc volume, 50 g of anhydrous crystalline glucose, 5.0 g of "NAFION" powder and 175 g of ethyl alcohol were charged and the reaction was effected at 130° C. for 30 minutes while stirring at 600 r.p.m. The pressure was 5.0–5.5 Kg/cm$^2$ (gauge pressure). After cooling to room temperature, "NAFION" was separated by filtration whereby a colorless, transparent ethyl glucoside solution was obtained.

By estimation of glucose by liquid chromatography and enzymatic method, the composition of the solid matters was found to be the following:

|  | composition by weight | molar yield |
|---|---|---|
| ethyl-α-glucoside | 51.8% by weight | 51.0 mol % |
| ethyl-β-glucoside | 29.7 by weight | 29.0 mol % |
| ethyl-α-maltoside & ethyl-β-maltoside | 12.3 by weight | 13.7 mol % |
| dextrose | 2.0 by weight | 2.3 mol % |
| higher oligoside, and others | 4.2 by weight | |
|  | 100.0 | |

EXAMPLE 7

In an autoclave of 500 cc volume, 50 g of anhydrous crystalline glucose, 5.0 g of "NAFION" powder and 200 g of n-butyl alcohol were charged and the reaction was effected at 135° C. for 1 hour while stirring at 600 r.p.m. After cooling to room temperature, "NAFION" was separated by filtration whereby a butyl glucoside solution was obtained.

By liquid chromatography and enzymatic method, the composition of the solid matters was found to be the following:

|  | molar yield |
|---|---|
| butyl-α-glucoside | 50.1 mol % |
| butyl-β-glucoside | 27.8 mol % |
| butyl-α-maltoside & butyl-β-maltoside | 15.2 mol % |
| dextrose | 2.7 mol % |
| higher oligoside, and others | 4.2 |
|  | 100.0 |

EXAMPLE 8

In a glass-lined autoclave of 1 l volume, 120 g of potato starch (containing 18.3% of moisture), 12.0 g of a perfluorosulfonic acid resin ("NAFION" powder) and 395 g of methyl alcohol containing 1.98 g (2% by weight in relation to dry starch) of hydrogen chloride were charged. The reaction was effected at 120° C. for 2 hours while stirring at 600 r.p.m. The pressure inside the system was 6.0 Kg/cm$^2$ (gauge pressure). After cooling to room temperature, "NAFION" was separated by filtration whereby a pale yellow methanolic solution of methyl glucoside was obtained. The solution was passed through a column filled with Amberlite A-21 to remove hydrochloric acid, and then, after addition of water, methyl alcohol was evaporated at 40° C. under reduced pressure whereby an aqueous methyl glucoside solution was obtained. In the aqueous solution 116 g of solid matters were contained. By means of liquid chromatography and enzymatic method, the solid matters were found to have the following composition and molar yield:

|  | composition by weight | molar yield |
|---|---|---|
| methyl-α-glucoside | 57.7% by weight | 57.1 mol % |
| methyl-β-glucoside | 30.0 by weight | 29.4 mol % |
| methyl-α-maltoside & methyl-β-maltoside | 6.8 by weight | 7.3 mol % |
| dextrose | 2.5 by weight | |
| higher oligoside, and others | 3.0 | |
|  | 100.0 | |

COMPARATIVE EXAMPLE 1

In an autoclave, 50 g (0.2778 mol) of anhydrous crystalline glucose, 12.5 g of "DIAION" sk1B (25% by weight in relation to glucose) and 125 ml (99 g) of methyl alcohol were reacted at 110° C. for 2 hours while stirring. After separation of the ion-exchange resin by filtration, a yellow glucoside solution was obtained. By estimation, the solid matters contained in the solution were found to have the following composition:

|  | molar yield |
|---|---|
| methyl-α-glucoside | 55.3 mol % |
| methyl-β-glucoside | 25.0 mol % |
| methyl-α-maltoside & methyl-β-maltoside | 9.8 mol % |
| dextrose | 4.9 mol % |
| ash, and others | 5.0 mol % |
|  | 100.0 |

What is claimed is:

1. A process for the preparation of glycosides which comprises reacting a monosaccharide or a polysaccharide with a monohydric alcohol or a polyhydric alcohol in the presence of a perfluorosulfonic acid at a temperature from above the boiling point of the alcohol to not more than 230° C.

2. A process according to claim 1 wherein the monosaccharide is glucose, mannose, galactose, arabinose, xylose or ribose.

3. A process according to claim 1 wherein the monosaccharide is glucose.

4. A process according to claim 1 wherein the polysaccharide is maltose, cellobiose, sucrose, lactose, oligosaccharide, dextrin, starch or cellulose.

5. A process according to claim 1 wherein the polysaccharide is dextrin or starch.

6. A process according to claim 1 wherein the monohydric alcohol is methyl alcohol, ethyl alcohol, propyl alcohol, isopropyl alcohol, butyl alcohol, amyl alcohol, 2-ethylhexyl alcohol, phenol or octyl alcohol.

7. A process according to claim 1 wherein the monohydric alcohol is methyl alcohol, ethyl alcohol or octyl alcohol.

8. A process according to claim 1 wherein the polyhydric alcohol is ethylene glycol, propylene glycol, butylene glycol or glycerol.

9. A process according to claim 1 wherein the polyhydric alcohol is ethylene glycol, propylene glycol or glycerol.

10. A process according to claim 1 wherein the amount of perfluorosulfonic acid resin is 5 to 20% by weight, in relation to the amount of the monosaccharide or the polysaccharide.

11. A process according to claim 1 wherein the reaction is conducted at a temperature between 100° C. and 150° C. in a tightly closed reaction vessel.

12. A process according to claim 1 wherein when a polysaccharide is used, hydrochloric acid is added in an amount of 1-2.5% by weight in relation to the amount of the polysaccharide.

13. A process according to claim 1 wherein the polysaccharide is a carbohydrate capable of yielding a monosaccharide by hydrolysis.

14. A process according to claim 1 wherein the alcohol is present in an excess with respect to the monosaccharide or polysaccharide.

15. A process according to claim 14 wherein the molar ratio of alcohol to saccharide is from about 3-50:1.

16. A process according to claim 1 wherein the reaction is conducted for about 10 minutes to about 3 hours.

* * * * *